US00PP37726P2

(12) United States Plant Patent
Pulte

(10) Patent No.: US PP37,726 P2
(45) Date of Patent: Oct. 6, 2026

(54) ***HIBISCUS* PLANT NAMED 'TNY049'**

(50) Latin Name: ***Hibiscus* hybrid (L.)**
Varietal Denomination: TNY049

(71) Applicant: UNIVERSITY OF TENNESSEE RESEARCH FOUNDATION, Knoxville, TN (US)

(72) Inventor: Andrew J. Pulte, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 19/361,562

(22) Filed: Oct. 17, 2025

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02
See application file for complete search history.

*Primary Examiner* — Kent L Bell
(74) *Attorney, Agent, or Firm* — SALIWANCHIK, LLOYD & EISENSCHENK

(57) ABSTRACT

A new distinct cultivar of winter-hardy, herbaceous, perennial, hybrid *Hibiscus* plant named 'TNY049' comprising a mounding habit with multiple mostly upright basal stems producing flowers along the top one-half to two-thirds of the plant. The plant blooms from mid-June through September with observable flowers often occurring in November. Flowers have overlapping petals that are edged in vibrant pink that dissolves into a lighter pink color gradient. Flowers have a deep shiny red eye. The foliage is mainly ovate with a crenate margin and acute leaf base. The tops of the leaves are forest green in color with lighter undersides. This new plant is useful in the landscape as a specimen plant or as part of a mixed border.

2 Drawing Sheets

Figure 1:
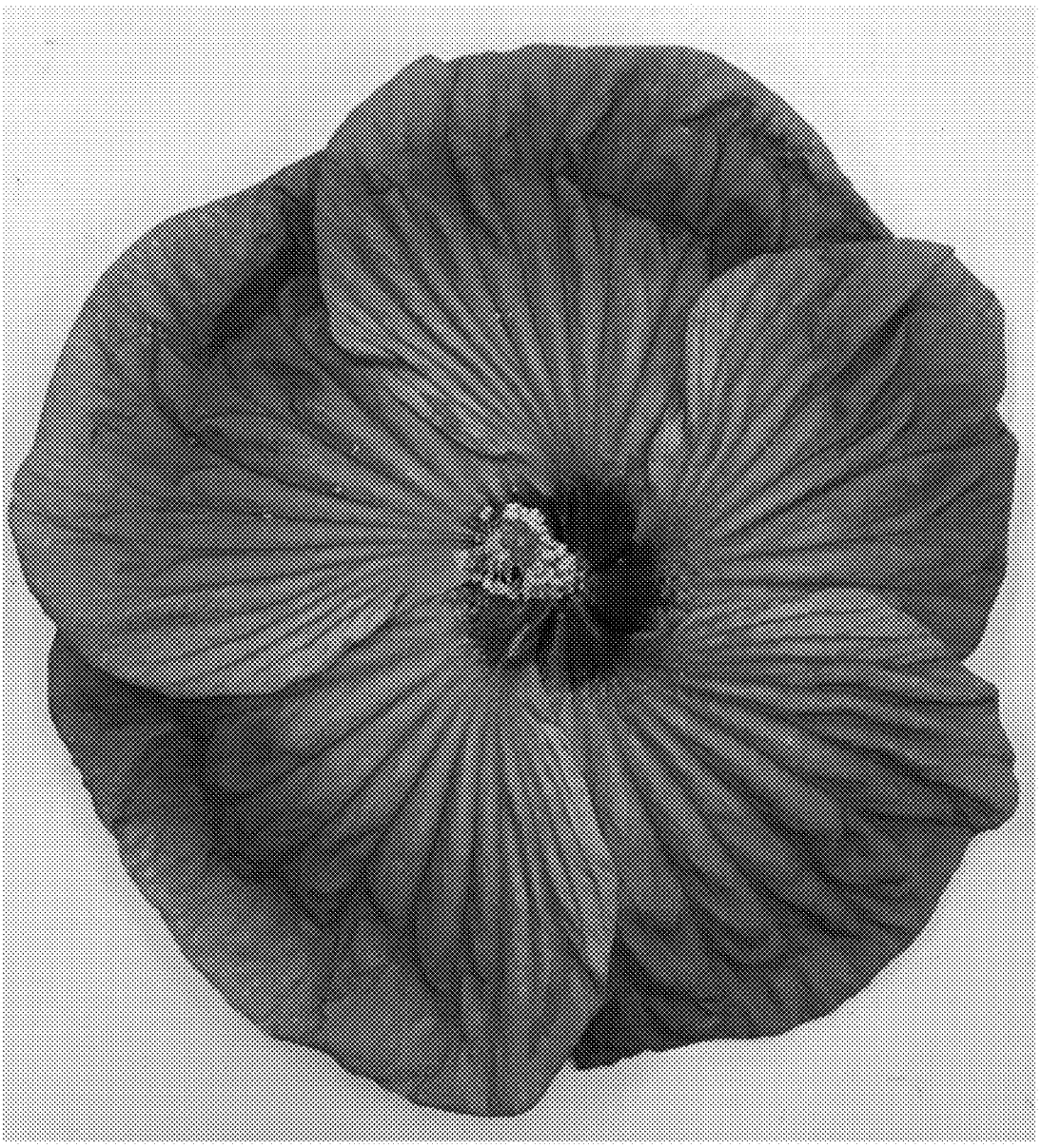

Botanical classification: *Hibiscus* hybrid (L.).
Cultivar denomination: 'TNY049'.

BACKGROUND AND ORIGIN OF THE PLANT

The present invention relates to a new and distinct cultivar of *Hibiscus,* which exhibits hardiness in, at least, USDA zones 7-9, unique flower color, and remontant blooming. This *Hibiscus* is botanically known as *Hibiscus* hybrid (L.) and is hereinafter referred to by the following cultivar name: 'TNY049'.

The new *Hibiscus* hybrid (L.) 'TNY049' is a product of the self-pollination of the unpatented proprietary plant *Hibiscus* hybrid (L.) 'TP017', and was developed by Dr. Andrew J. Pulte in Knoxville, Tennessee. The 'TP017' parent comprises a complex mixture of species, including at least the species: *Hibiscus moscheutos* and *Hibiscus coccineus*. The seedling 'TNY049' was selected in 2016 and has been evaluated through trials at The State Botanical Garden of Tennessee in Knoxville, Tennessee and a trial site in Loxley, Alabama.

'TNY049' was first asexually propagated in 2016 by cuttings harvested in Knoxville, Tennessee. The resultant asexually propagated plants have shown that the unique features of this new *Hibiscus* cultivar are stable and reproduced true-to-type in successive generations. Furthermore, the plant will not come true from seed; it can be truly reproduced only by asexual means. The original plant has been moved and is growing under controlled observation in Loxley, Alabama, and asexual reproduction of the new *Hibiscus* 'TNY049' using vegetative terminal cuttings in a controlled environment has been continued in Loxley, Alabama and Knoxville, Tennessee.

BRIEF SUMMARY OF THE PLANT

'TNY049' is a winter-hardy *Hibiscus,* which, to the knowledge of the inventor, differs in several traits from its parent as well as all other winter-hardy *Hibiscus,* including the most similar known to the inventor, which are as follows: *Hibiscus* hybrid (L.) 'Pink Elephant' (U.S. Plant Pat. No. 21,883) and *Hibiscus* hybrid (*moscheutos*) (L.) 'PAS490714' (unpatented), known as Luna™ Rose.

When compared with its parent, 'TP017', the 'TNY049' plant has a more vibrant flower color, thicker and stiffer leaves, and a stronger, sturdier upright habit.

When compared with 'Pink Elephant', the flowers of 'TNY049' are smaller, more vibrant in color, and more abundant.

When compared with 'PAS490714', the 'TNY049' plant is taller, the flower color is more vibrant, and the flowers are more abundant.

'TNY049' is a *Hibiscus* cultivar that has been observed to exhibit winter hardiness in USDA zones 7-9, and which was developed via manual/hand self-pollination in Knoxville, Tennessee. The plant will not come true from seed; it can be truly reproduced only by asexual means. It is also characterized by the following traits, which have been repeatedly observed and are determined to be the unique and distinguishing characteristics of the new *Hibiscus* cultivar named 'TNY049'. In combination, these traits set 'TNY049' apart from all other existing varieties of *Hibiscus* known to the inventor:

1. Large, dense, broadly globose form with strong vigor;
2. Attractive bright pink flowers with a red eyespot in a color pattern not observed by the inventor in known cultivars. Flowers have overlapped petals with light pink streaks between the ruffles of individual petals, giving a color gradient effect;
3. Dark green foliage on top of leaf with lighter undersides that are micro-puberulent;
4. Strong remontant flowering; and
5. Observed intermediate resistance to *Hibiscus* sawfly (*Atomacera decepta*), which is lacking in most existing known cultivars of *Hibiscus* hybrid (L.).

BRIEF DESCRIPTION OF THE PHOTOGRAPHS

FIG. 1. Photograph of a typical inflorescence of 'TNY049' depicting typical flower structure. Individual flowers average 20 cm in diameter exhibiting vibrant pink color that fades in a color gradient to very light pink toward the center of the flower. Colors in the photograph may differ from the actual colors due to lighting and light reflectance.

Figure 2:
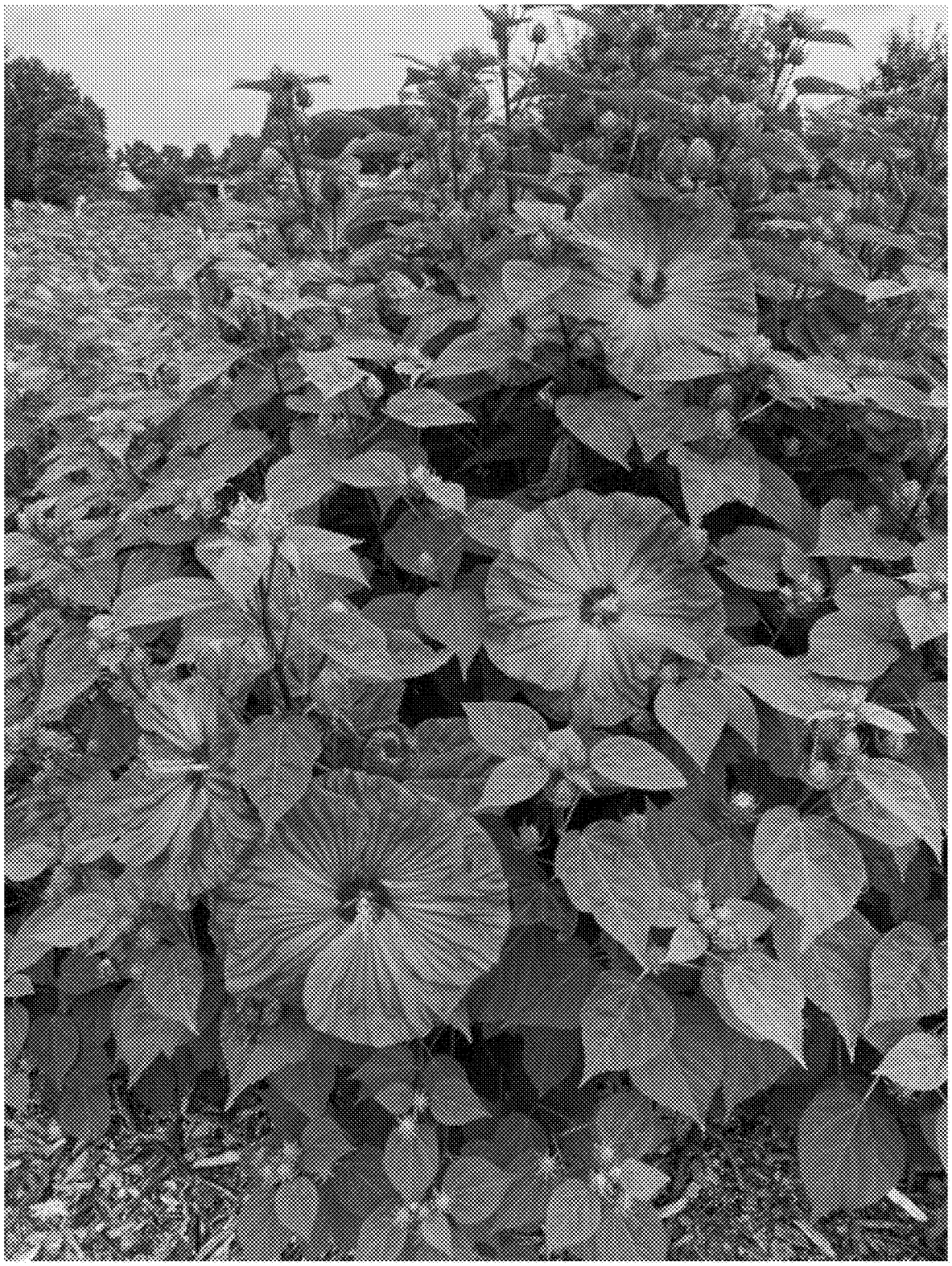

FIG. 2. Photograph of a 5 year-old plant in early stages of flowering in a trial garden.

DETAILED BOTANICAL DESCRIPTION

The following description uses color references to The Royal Horticultural Society Colour Chart (sixth edition), except where general terms of ordinary dictionary significance are used.

Continued observations of 'TNY049' asexually produced progeny have shown that the unique features of this new *Hibiscus* 'TNY049' are stable and reproduced true to type in successive generations. The new *Hibiscus* cultivar 'TNY049' has not been observed under all possible environmental conditions. The phenotype may vary somewhat with variations in environment and cultural practices such as temperature, water and fertility levels, soil types, and light intensity.

The following observations, measurements and comparisons describe this cultivar grown in Knoxville, Tennessee. *Hibiscus* plants used for this description were about 5 years old and planted in native soil in trial beds in full-sun. The claimed *Hibiscus* plant has been truly tested for hardiness in USDA zones 7-9; however, this *Hibiscus* is broadly recognized as being hardy in zones 4-9.

Botanical classification: *Hibiscus* hybrid (L.) 'TNY049'.

Parentage: Self-hybridization of *Hibiscus* hybrid (L.) 'TP017' (proprietary, unpatented).

Propagation:

*Type*.—Vegetative terminal cutting or divisions.

*Time to initiate roots*.—2.5 weeks, fully rooted in approximately 5 weeks; cuttings taken before flowering.

*Rooting habit*.—Dense; fibrous; fleshy.

*Root color*.—Milky yellow, nearest RHS 161D and lighter at the terminal end depending on soil type.

*Crop time*.—Under normal summer growing conditions, 13 to 16 weeks to flower in a four-liter container from cutting; plant vigor is average/intermediate.

Plant description:

*Plant form and growth habit*.—Hardy herbaceous perennial shrub, with broadly globose mounding habit.

*Growth habit*.—Mounding.

*Plant size*.—4'5" X 4'5" (134.62 cm X 134.62 cm).

*Vigor*.—Average/Intermediate.

*Branching habit*.—Upright, 15 to 20 thick upright branched main stems forming a broadly globose plant, 8 to 10 primary branches per main stem protruding at 60° to 45° angle from vertical; secondary branches are uncommon.

*Branch color*.—Main branch color at base between RHS 135D and RHS 136D with tinting in high light exposed portions nearest RHS 182B; distal portion between RHS 183A and RHS 187C.

*Main stem/trunk description*.—Terete; glabrous; glaucous.

*Internode description*.—Node spacing is variable depending on maturity of growth; spacing ranges from 2 cm to greater than 10 cm.

Foliage description:

*Arrangement*.—Alternate: there is one leaf per node along the stem.

*Leaf blade length* (*cm*).—10 to 14 cm.

*Leaf blade width* (*cm*).—8 to 10 cm.

*Leaf shape*.—Ovate.

*Apex*.—Acuminate.

*Base*.—Acute on immature foliage maturing to cordate.

*Margin*.—Crenate.

*Texture*.—Micro-puberulent under magnification, smooth to the naked eye.

*Leaf color* (*upper surface*).—Nearest to RHS 135D.

*Leaf color* (*lower surface*).—Nearest to RHS 136D.

*Leaf vein arrangement*.—Palmate, costate.

*Vein color* (*upper surface*).—Matte adaxial; color ranges between RHS 145A and RHS 145B.

*Vein color* (*lower surface*).—Matte abaxial; color ranges between RHS 145A and RHS 145B.

*Petioles*.—4 to 11 cm long and 5 mm in diameter; glaucous; glabrous to the naked eye but micro-puberulent under magnification; nearly round to concave on top surface near base; color ranges between RHS 145A and RHS 145B.

*Trichomes*.—Micro-puberulent under magnification.

Flower description:

*Fragrance*.—None.

*Flower bud description*.—Solitary, ovoid to broadly ovoid, color nearest RHS 135D.

*Flower bud size*.—2 cm in length and 2 cm in diameter on previous day before flowering.

*Natural flowering season*.—Plant blooms from mid-June through September with observable flowers often occurring in November.

*Flower lastingness*.—1 to 2 days.

*Inflorescence width* (*fully open*).—20 cm.

*Sepals*.—Five; micro-puberulent; acute apex; fused base; margin entire, edentate; abaxial and adaxial surfaces matte; about 3.0 cm long, fused in about the basal 1.0 cm, about 2.0 cm wide at fusion; connate forming campanulate star-shaped calyx; upper surface color nearest RHS 135D; lower surface color nearest RHS 135D.

*Flower number*.—Mature plants can produce in excess of 200 individual flowers during the growing season.

*Flower arrangement*.—Solitary.

*Petal description*.—Five overlapping petals form rotate inflorescence (petals overlapping 25%); margins: entire, edentate; apex: rounded; base: short claw-like; individual petals are fan shaped and approximately 10 cm in both length and broadest width, together form a 20 cm wide inflorescence (size reduced in later part of flowering season); petals are textured on abaxial and adaxial surface, slight luster, palmately veined, primary veins impressed on adaxial and slightly costate abaxial; surface slightly dimpled.

*Petal color*.—When opening and fully opened, upper (inner) surface: distally, between RHS 63B and RHS 63C, fading to RHS 49D at the central part of the petal; when opening and fully opened, lower (outer) surface: distally, close to RHS 63C fading to RHS 63D and proximally, close to RHS 155D.

*Bracts*.—Number varies, very often 10 per flower; linear; entire, with margin micro-ciliolate; micro-puberulent, dull surfaces both abaxial and adaxial; sharply acute apex and truncate base; arcuate upwards near apex; about 26 mm long and about 3.5 mm wide at base.

*Gynoecium*.—Style: Enclosed in column; light pink, lighter than RHS 36D; 5 to 7 cm long and 2 mm diameter; split into five branches in the distal 12 to 15 mm; Stigma: Color nearest RHS 35D; typically, five; globose, flattened proximally, puberulent; about 3 mm in diameter and 1 mm tall; Ovary: Superior; cone with a slightly flattened top; longitudinally grooved in undulated pattern; rounded apex and truncate base; about 8 mm across at base and about 8 mm tall; color nearest RHS 145C.

*Androecium*.—Filaments: Numerous, about 125; less than 1 mm in diameter and about 5 mm long; attached to entire length of column; near anther color nearest RHS 56B, fading to lighter pink nearest RHS 65D; Anthers: Orbicular but irregular during anthesis, about 2 mm in diameter on the round side and 1 mm thick; before anthesis variable color but nearest RHS 47D on the perimeter and in the center; Pollen: Numerous; round with microscopic points; shiny; less than 0.1 mm long; color nearest RHS 27D but slightly lighter.

*Pedicel*.—Micro-puberulent; rounded; very slightly curved; length from base of bud to abscission point about 2.0 cm long and 4 mm wide; color nearest RHS 132C.

*Peduncle*.—Terete; cylindrical; micro-puberulent; flowers held outwardly facing and are easily visible by up to 6 cm long and 3 mm wide; micro-puberulent; color ranges between RHS 145A and RHS 145B.

Fruit description:

*Fruit type*.—Five-valved (penta-loculicidal) capsule, longitudinally dehiscing; pubescent along inner septa, micro-puberulent outside; ellipsoidal, cuspidate apex and flattened base; about 3 cm long and 2 cm diameter.

*Fruit color* (*when mature*).—Color nearest RHS 200C when mature.

*Seed description*.—Minutely floccose; globose to slightly reniform; about 2.4 mm to 3 mm in diameter; color nearest RHS 200B.

Disease resistance: Disease resistance beyond that of other hardy *Hibiscus* has not been observed.

Pest resistance: Observed to exhibit intermediate resistance to *Hibiscus* sawfly (Atomacera decepta) under field conditions.

Other unique attributes: This cultivar exhibits unique flower color, and remontant blooming. Some individual flowers have variable light pink streaking nearest RHS 62C not observed in every flower.

I claim:

1. A new and distinct cultivar of *Hibiscus, Hibiscus* hybrid (L.), named 'TNY049', as illustrated and described.

* * * * *